US007723024B2

(12) United States Patent
Dawes et al.

(10) Patent No.: US 7,723,024 B2
(45) Date of Patent: May 25, 2010

(54) METHOD OF MONITORING A FERMENTATION PROCESS

(75) Inventors: Ian Dawes, Coogee (AU); Vincent James Higgins, Rydalmere (AU); Peter John Rogers, Williamstown (AU)

(73) Assignee: Unisearch Limited, Sydney (AU)

( * ) Notice: Subject to any disclaimer, the term of this patent is extended or adjusted under 35 U.S.C. 154(b) by 383 days.

(21) Appl. No.: 10/477,834

(22) PCT Filed: May 15, 2002

(86) PCT No.: PCT/AU02/00595

§ 371 (c)(1),
(2), (4) Date: Apr. 7, 2004

(87) PCT Pub. No.: WO02/092846

PCT Pub. Date: Nov. 21, 2002

(65) Prior Publication Data

US 2004/0157228 A1    Aug. 12, 2004

(30) Foreign Application Priority Data

May 15, 2001    (AU)    ................................ PR5010

(51) Int. Cl.
*C12Q 1/68*    (2006.01)
*C07H 21/04*    (2006.01)
(52) U.S. Cl. .................... 435/6; 435/91.2; 536/23.1; 536/24.32
(58) Field of Classification Search ....................... None
See application file for complete search history.

(56) References Cited

OTHER PUBLICATIONS

Lyons, Thomas et al. Genome wide characterization of the Zap1p zinc responsive regulon in yeast. 2000. PNAS vol. 97, No. 14, 7957-7962.*
Bromberg, Susan et al. Requirments for Zinc, Manganese, Calcium, and Magnesium in Wort. 1997. American Society of Brewing Chemists. vol. 55 pp. 123-128.*
NCBI Entrez Gene website search results for YOR387C and YGL258W. See attachment.*
De Risi, Joseph et al. Exploring the Metabolic and Genetic Control of Gene Expression on a Genomic Scale. 1997. Science. vol. 278 pp. 680-686.*
Daniel S. Yuan, "Zinc-Regulated Genes in *Saccharomyces cerevisiae* Revealed by Transposon Tagging," Genetics Society of America, Sep. 2000, pp. 45-58.
Gil-Soo Han et al., "Regulation of the *Saccharomyces cerevisiae* DPPI-Encoded Diacylglycerol Pyrophosphate Phosphatase by Zinc," The Journal of Biological Chemistry, Mar. 30, 2001, pp. 10126-10133, vol. 276, No. 13.
Old Yellow Enzyme. The discovery of multiple isozymes and a family of related proteins. J Biol Chem., 2680, 6097-106 Scott K, Saito K, Thiele DJ, Massey V. (1993).
Regulatory elements that control transcription activation and unsaturated fatty acid-mediated repression of the *Saccharomyces cerevisiae* OLE1 gene. J Biol Chem., 271, 3581-9, Choi, J.Y., Stukey, L, Hwang, S.Y., and Martin, C.E. (1996).
Molecular cloning and characterization of 12-oxophytodienoate reductase, an enzyme of the octadecanoid signaling pathway from *Arabidopsis thaliana*. Structural and functional relationship to yeast old yellow enzyme. J. Biol. Chem., 272, 28066-72, Schaller F, Weiler EW. (1997).
Exploring the Metabolic and Genetic Control of Gene Expression on a Genomic Scale. Science, 278, 680-686. DeRisi, J.L., Iyer, V.R., and Brown, P.O. (1997).
Zap1p, a Metalloregulatory Protein Involved in Zinc-Responsive Transcriptional Regulation in *Saccharomyces cerevisiae*, Mol Cell Biol. 17, 5044-52, Zhao, H. And Eide, D.J. (1997).
Cytochrome P450 Enzyme Systems in Fungi Genet. Biol. 23, 1-17. van den Brink, H.M., van Gorcom, R.F., van den Hondel, CA., and Punt, P.J. (1998).
Transcriptional CO-regulation of *Saccharomyces cerevisiae* Alcohol Acetyltransferase Gene, ATF1 and Ä-9 Fatty Acid Desaturase Gene. OLE1 by Unsaturated Fatty Acids. Yeast, 14,711-721, Fujiwara, D., Yoshimoto, R, Sibe, R, Harashima S. and Tamai, Y. (1998).
Biochemistry, Cell Biology and Molecular Biology of Lipids of *Saccharomyces cerevisiae*. Yeast, 14, 1471-1510. Daum, G., Lees, N. D., Bard, M. and Dickson, R. (1998).
A Genome-Wide Transcriptional Analysis of the Mitotic Cell Cycle, Molecular Cell, vol. 2, 65-7.
An Inverse Correlation between Stress Resistance and Stuck Fermentations in Wine Yeasts. A Molecular Study Biotechnol and Bioengineering. 64,698-708. lvorra, C, Perez-Ortin, J.E, del Olmo, M. (2000).
Zinc Deficiency Induces Oxidative Stress and AP-1 Activation in 3T3 Cells, Free Radical Biology and Medicine, 28, 1091-1099. Oteiza, P. L, Clegg, M. S., Zago, M. P., Keen, C.L. (2000).
Stress response and expression patterns in wine fermentations of yeast genes induced at the diauxic shift. Yeast, 16, 139-148. Puig, S., and Perez-Ortin, J.E. (2000).
O2R, a Novel Regulatory Element Mediating Rox1p-Independent 02 and Unsaturated Fatty Acid Repression of OLE1 in *Saccharomyces cerevisiae*. J. Bacteriol., 183,745-751. Nakagawa, Y, Sugioka, S, Kaneko, Y, and Harashima, S. (2001).
Higgins VJ, Rogers PJ, Dawes IW, Application of genome-wide expression analysis to identify molecular markers useful in monitoring industrial fermentations., 2003, *Appl Environ Microbiol.* 69:7535-40.
S.L. Tai et al., Two-Dimensional Transcriptome Analysis in Chemostat Cultures, 2005, *J. Biol Chem.* 280:437-47.

* cited by examiner

*Primary Examiner*—Stephen Kapushoc
*Assistant Examiner*—Amanda Shaw
(74) *Attorney, Agent, or Firm*—Browdy and Neimark, PLLC

(57) ABSTRACT

This invention relates to a method of monitoring a fermentation process. In particular, the invention relates to a method of monitoring a fermentation process comprising the step of measuring the expression level of one or more zinc regulated nucleic acid molecules from a microorganism, preferably selected from the group consisting of *Escherichia Bacillus, Cyanobacter, Streptomyces, Corynebacteria, Zymomonas, Saccharomyces, Zygosaccharomyces*, and *Schizosaccharomyces* cells, present in the fermentation and comparing the expression level to a reference level of expression for the nucleic acid molecules, wherein the expression level is indicative of sub-optimal fermentation. Preferably the fermentation process is a beer brewing process.

3 Claims, 5 Drawing Sheets

```
MSFLNIFTFFSVLVSVATAVRFDLTNVTCNNLHGPHCGTYVMEVVGQNGTFLGQSTFAGA
MSFL+IFTFFSVL+SVAT VRFDLTNVTC  LHGPHCGTYVMEVVGQNGTFLGQSTF GA
MSFLSIFTFFSVLISVATTVRFDLTNVTCKGLHGPHCGTYVMEVVGQNGTFLGQSTFVGA

DVLTESAGDAWARYLGQETRFLPKLTTIASNDTKNFSPLIFTTNIYTCNPQSIGDAMVPF
DVLTESAGDAWARYLGQETRFLPKLTTIASN+TKNFSPLIFTTNI TCNPQSIGDAMVPF
DVLTESAGDAWARYLGQETRFLPKLTTIASNETKNFSPLIFTTNINTCNPQSIGDAMVPF

ANTVTGEIEYNSWADTADNASFITGLANQLFNSTQYGVQVASCYPNFASVILSTPTVNIF
ANTVTGEIEYNSWADTADNASFITGLANQLFNST YGVQVASCYPNFASVILSTP VNIF
ANTVTGEIEYNSWADTADNASFITGLANQLFNSTDYGVQVASCYPNFASVILSTPAVNIF

AANETLPDYCTAIQLKAVCPPDAGF
  ++TLPDYCTAIQLKAVCPP+AGF
GKDDTLPDYCTAIQLKAVCPPEAGF
```

FIGURE 2

```
TATTACGGCAGTTTTTTTGGACTGGGTCAAAAAAAGTGTTGCATAATCAA
CATTACGGCAGTTTTTT  GGACTGGGTCAAAAAAAGTGTTGCATAATCAA

ATCAGGAACACATTAAAATGTTGTAAAATTTGTCTTAGTATCACCTGAGT
ATCAGGAACACATTAAAATGTTATAAAATTTGTCTTAGTATGACCTGAGT

GGTTATTCATTACGTACTACTGTCAAAATATTCGGATCTTTCCTAAACGG
GGTTATTCATTACGTACTACTGTCAAAATATTCGGATCTTTCCTAAACGG

GCTTTTGAATTAGTGTTGCTTCTATTCCTGGAATGGAAGGTAATACTTTC
GCTTTTGAATTAGTGTTGCTTCTATTCCTGGAATGGAAGGTAGTAATTTC

ATGCATTCTCGCTTTTCGGACTTTTAACAATAAATTAAAAACAATGATAC
ATGCATTCTCGCTTTTCGGACTTTTAACAATAAATTAAAAACAATGATAC

TTTCATCAACTACCTATACACCCTGCGGGTCAATTATTTTTTTTT CGAAT
TTTCATCAACTACCTATACACCCTGCGGGTCAATTATTTTTTTTTCGAAT

AACCGCTGAGGTTGGAAATATAGAAACATATTCCAGATCTGTATTTTCAG
AACCGCTGAGGTTGGAAATATAGAAACATATTCCAGATCTGTATTTTCAG

TTGCTAGAAAAAGGTTAATATAATCATTAAGGTTTTCAGCATATAACAGG
TTGCTAGAAAAAGGTTAATATTATCATTAAGGTTTTCAGCATATAACAGG

TATAATTGATATATAAGCATCGTAATTTTCATTCAAAATGGAGAGCTACT
TATAATTGATATATAAGCATCGTAATTTTCATTCAAAATGGAGAGCTACT

GCTTCTGATAGATTGTACAATCTCAAGAAATCAAGAACAACAACCATACC
GCTTCTGATAGATTGTACAATCTCAAGAAATCAAGAACAACAACCATACC

TTTTTTCCAGCTGCATAATCTGTAGACATATTTAAGTATATTTTTTAGG
TCTTTTCTCACATCCTCACTTATAGATATGTTTTGATTATTTTCGTTATA

CAGTTTTATAAATTAACAGACTATAATTATTTTAGAGAAAAAGACCCAGA
GACAAAAATCTTTTGAGAAAGCCATGCGGAAGTTATTTTTAACTGTAAAG

TTTATACTTCTGACTTTTCTTTTTTATGTTGATCTTATTGTCACTGTCAT
TACAATCGATTTCCTTTAGGCATTTCTACTTTCTTCTGACCCTGATTTAA

TGGATCATAATAATGATTCTTTTTTGAAC
AATTTTCGAGTTCTTTTTGTTACGATGCG
```

FIGURE 3

SEQUENCE LISTING

```
<160> NUMBER OF SEQ ID NOS: 7

<210> SEQ ID NO 1
<211> LENGTH: 36
<212> TYPE: DNA
<213> ORGANISM: Saccharomyces cerevisiae
```

<400> SEQUENCE: 1
ataagaatgc ggccgctgtt ttggcgtatt ctccac                36

<210> SEQ ID NO 2
<211> LENGTH: 29
<212> TYPE: DNA
<213> ORGANISM: Saccharomyces cerevisiae

<400> SEQUENCE: 2
ccgctcgaga acacgcgtaa ttgaaaggg                29

<210> SEQ ID NO 3
<211> LENGTH: 205
<212> TYPE: PRT
<213> ORGANISM: Saccharomyces cerevisiae

<400> SEQUENCE: 3

Met Ser Phe Leu Asn Ile Phe Thr Phe Phe Ser Val Leu Val Ser Val
1               5                   10                  15

Ala Thr Ala Val Arg Phe Asp Leu Thr Asn Val Thr Cys Asn Asn Leu
            20                  25                  30

His Gly Pro His Cys Gly Thr Tyr Val Met Glu Val Val Gly Gln Asn
        35                  40                  45

Gly Thr Phe Leu Gly Gln Ser Thr Phe Ala Gly Ala Asp Val Leu Thr
    50                  55                  60

Glu Ser Ala Gly Asp Ala Trp Ala Arg Tyr Leu Gly Gln Glu Thr Arg
65                  70                  75                  80

Phe Leu Pro Lys Leu Thr Thr Ile Ala Ser Asn Asp Thr Lys Asn Phe
                85                  90                  95

Ser Pro Leu Ile Phe Thr Thr Asn Ile Tyr Thr Cys Asn Pro Gln Ser
            100                 105                 110

Ile Gly Asp Ala Met Val Pro Phe Ala Asn Thr Val Thr Gly Glu Ile
        115                 120                 125

Glu Tyr Asn Ser Trp Ala Asp Thr Ala Asp Asn Ala Ser Phe Ile Thr
    130                 135                 140

Gly Leu Ala Asn Gln Leu Phe Asn Ser Thr Gln Tyr Gly Val Gln Val
145                 150                 155                 160

Ala Ser Cys Tyr Pro Asn Phe Ala Ser Val Ile Leu Ser Thr Pro Thr
                165                 170                 175

Val Asn Ile Phe Ala Ala Asn Glu Thr Leu Pro Asp Tyr Cys Thr Ala
            180                 185                 190

Ile Gln Leu Lys Ala Val Cys Pro Pro Asp Ala Gly Phe
        195                 200                 205

<210> SEQ ID NO 4
<211> LENGTH: 190
<212> TYPE: PRT
<213> ORGANISM: Saccharomyces cerevisiae

<400> SEQUENCE: 4

Met Ser Phe Leu Ile Phe Thr Phe Phe Ser Val Leu Ser Val Ala Thr
1               5                   10                  15

Val Arg Phe Asp Leu Thr Asn Val Thr Cys Leu His Gly Pro His Cys
            20                  25                  30

Gly Thr Tyr Val Met Glu Val Val Gly Gln Asn Gly Thr Phe Leu Gly
        35                  40                  45

-continued

```
Gln Ser Thr Phe Gly Ala Asp Val Leu Thr Glu Ser Ala Gly Asp Ala
 50                  55                  60

Trp Ala Arg Tyr Leu Gly Gln Glu Thr Arg Phe Leu Pro Lys Leu Thr
 65                  70                  75                  80

Thr Ile Ala Ser Asn Thr Lys Asn Phe Ser Pro Leu Ile Phe Thr Thr
                 85                  90                  95

Asn Ile Thr Cys Asn Pro Gln Ser Ile Gly Asp Ala Met Val Pro Phe
            100                 105                 110

Ala Asn Thr Val Thr Gly Glu Ile Glu Tyr Asn Ser Trp Ala Asp Thr
        115                 120                 125

Ala Asp Asn Ala Ser Phe Ile Thr Gly Leu Ala Asn Gln Leu Phe Asn
    130                 135                 140

Ser Thr Tyr Gly Val Gln Val Ala Ser Cys Tyr Pro Asn Phe Ala Ser
145                 150                 155                 160

Val Ile Leu Ser Thr Pro Val Asn Ile Phe Thr Leu Pro Asp Tyr Cys
                165                 170                 175

Thr Ala Ile Gln Leu Lys Ala Val Cys Pro Pro Ala Gly Phe
            180                 185                 190
```

<210> SEQ ID NO 5
<211> LENGTH: 679
<212> TYPE: DNA
<213> ORGANISM: Saccharomyces cerevisiae

<400> SEQUENCE: 5

```
tattacggca gttttttggg actgggtcaa aaaagtgtt gcataatcaa atcaggaaca      60
cattaaaatg ttgtaaaatt tgtcttagta tcacctgagt ggttattcat tacgtactac    120
tgtcaaaata ttcggatctt tcctaaacgg cttttgaat tagtgttgct tctattcctg     180
gaatggaagg taatactttc atgcattctc gcttttcgga cttttaacaa taaattaaaa    240
acaatgatac tttcatcaac tacctataca ccctgcgggt caattatttt tttttcgaat    300
aaccgctgag gttggaaata tagaaacata ttccagatct gtattttcag ttgctagaaa    360
aaggttaata taatcattaa ggttttcagc atataacagg tataattgat atataagcat    420
cgtaattttc attcaaaatg gagagctact gcttctgata gattgtacaa tctcaagaaa    480
tcaagaacaa caaccatacc ttttttccag ctgcataatc tgtagacata ttttaagtat    540
atttttttagg cagttttata aattaacaga ctataattat tttagagaaa aagacccaga    600
tttatacttc tgactttttct tttttatgtt gatcttattg tcactgtcat tggatcataa    660
taatgattct ttttttgaac                                                 679
```

<210> SEQ ID NO 6
<211> LENGTH: 678
<212> TYPE: DNA
<213> ORGANISM: Saccharomyces cerevisiae

<400> SEQUENCE: 6

```
cattacggca gttttttgga ctgggtcaaa aaaagtgttg cataatcaaa tcaggaacac      60
attaaaatgt tataaaattt gtcttagtat gacctgagtg ttattcatt acgtactact     120
gtcaaaatat tcggatcttt cctaaacggg cttttgaatt agtgttgctt ctattcctgg    180
aatggaaggt agtaatttca tgcattctcg cttttcggac ttttaacaat aaattaaaaa    240
caatgatact ttcatcaact acctatacac cctgcgggtc aattattttt tttttcgaat    300
aaccgctgag gttggaaata tagaaacata ttccagatct gtattttcag ttgctagaaa    360
```

-continued

```
aaggttaata ttatcattaa ggttttcagc atataacagg tataattgat atataagcat    420
cgtaattttc attcaaaatg gagagctact gcttctgata gattgtacaa tctcaagaaa    480
tcaagaacaa caaccatacc tcttttctca catcctcact tatagatatg ttttgattat    540
tttcgttata gacaaaaatc ttttgagaaa gccatgcgga agttattttt aactgtaagt    600
acaatcgatt tcctttaggc atttctactt tcttctgacc ctgatttaaa attttcgagt    660 tcttttttgtt acgatgcg                                                 678
```

<210> SEQ ID NO 7
<211> LENGTH: 205
<212> TYPE: PRT
<213> ORGANISM: Saccharomyces cerevisiae

<400> SEQUENCE: 7

```
Met Ser Phe Leu Ser Ile Phe Thr Phe Phe Ser Val Leu Ile Ser Val
1               5                   10                  15

Ala Thr Val Arg Phe Asp Leu Thr Asn Val Thr Cys Lys Gly Leu
            20                  25                  30

His Gly Pro His Cys Gly Thr Tyr Val Met Glu Val Val Gly Gln Asn
        35                  40                  45

Gly Thr Phe Leu Gly Gln Ser Thr Phe Val Gly Ala Asp Val Leu Thr
    50                  55                  60

Glu Ser Ala Gly Asp Ala Trp Ala Arg Tyr Leu Gly Gln Glu Thr Arg
65                  70                  75                  80

Phe Leu Pro Lys Leu Thr Thr Ile Ala Ser Asn Glu Thr Lys Asn Phe
                85                  90                  95

Ser Pro Leu Ile Phe Thr Thr Asn Ile Asn Thr Cys Asn Pro Gln Ser
            100                 105                 110

Ile Gly Asp Ala Met Val Pro Phe Ala Asn Thr Val Thr Gly Glu Ile
        115                 120                 125

Glu Tyr Asn Ser Trp Ala Asp Thr Ala Asp Asn Ala Ser Phe Ile Thr
    130                 135                 140

Gly Leu Ala Asn Gln Leu Phe Asn Ser Thr Asp Tyr Gly Val Gln Val
145                 150                 155                 160

Ala Ser Cys Tyr Pro Asn Phe Ala Ser Val Ile Leu Ser Thr Pro Ala
                165                 170                 175

Val Asn Ile Phe Gly Lys Asp Asp Thr Leu Pro Asp Tyr Cys Thr Ala
            180                 185                 190

Ile Gln Leu Lys Ala Val Cys Pro Pro Glu Ala Gly Phe
        195                 200                 205
```

METHOD OF MONITORING A FERMENTATION PROCESS

This application is the U.S. National Phase of PCT Application PCT/AU02/00595 filed on 15 May 2002 which claims priority from Australian Provisional Application PR 5010 which was filed on 15 May 2001.

FIELD OF THE INVENTION

This invention relates to a method of monitoring a fermentation process. In particular the invention relates to a method of monitoring a fermentation process comprising the step of measuring the expression level of a gene or genes of a microorganism present in the fermentation, wherein said expression level is indicative of sub-optimal fermentation. The invention further relates to genes or gene products affected by, or associated with, fermentation.

BACKGROUND OF THE INVENTION

Fermentation processes are hostile environments for microorganisms such as yeast, subjecting them to numerous stresses. These stresses can lead to defective or sub-optimal fermentation in which yeast metabolism is halted and/or undesirable flavours are produced (Ivorra et. al., 1999).

While the major requirements for successful fermentation have been identified though previous research efforts, there are no recognised tools that allow the rapid detection of the source of fermentation problems early enough to circumvent them. Indeed, the majority of industrial fermentations are monitored purely by the assessment of the specific gravity of the fermentation medium. Accordingly, in an attempt to overcome or at least alleviate some of the problems associated with monitoring fermentation the applicant proposes utilising molecular techniques to identify genes which are indicative of sub-optimal fermentation. In particular the applicant proposes using molecular methods to monitor the in vivo effects of varying fermentation conditions so that a more accurate assessment of the effect of these conditions on the microorganisms present during fermentation can be undertaken.

Until recently the rate limiting step in the development of methods for monitoring fermentation was the identification of suitable genes. However, the applicant has now found that by using genome-wide transcriptional analysis, genes can be identified that meet the methods' requirements. Therefore, the applicant proposes that the use of this technique can readily determine which genes are highly responsive and specific to defined stresses, such as zinc-limiting conditions. Having identified potentially useful genes, their "normal" levels of expression can be determined so that an accurate assessment of sub-optimal expression levels can be identified during fermentation.

Genes that may be of use include HSP12 (Ivorra et. al., 1999) and SPI1 (Puig and Perez-Ortin, 2000) which have been shown to have promise as genetic markers for stress conditions in alcoholic fermentation. While these genes respond to a broad range of sub-optimal conditions and allow the identification of the presence of stress per se, their non-specificity prevents their use to identify the cause or type of stress.

Zinc deficiency, for instance, is a major contributor to the retardation of yeast fermentation in the beer brewing process (Bromberg et. al., 1997). The lack of available zinc slows down the fermentation rate, even leading to the complete cessation of fermentation or a "stuck brew". The direct measurement of zinc levels in wort is not a reliable measure of zinc deficiency, since zinc can be present in a form that is not available to the yeast.

The applicant has accordingly further identified a gene whose expression levels are directly affected by the presence of zinc. The applicant proposes that this gene will be useful for monitoring a fermentation process for zinc deficiency.

It will be appreciated by those skilled in the art that there are a number of techniques that can be used to determine the level of gene expression. For example, Northern hybridisation analysis, dot blots and real-time polymerase chain reaction.

It will be clearly understood that, although a number of prior art publications are referred to herein, this reference does not constitute an admission that any of these documents form part of the common general knowledge in the art, in Australia or in any other country.

SUMMARY OF THE INVENTION

In its most general aspect, the invention disclosed herein provides a method of monitoring a fermentation process whereby sub-optimal fermentation is more readily identified than by using standard techniques.

Accordingly, in a first aspect, the present invention provides a method of monitoring a fermentation process comprising the step of measuring the expression level of a one or more nucleic acid molecules from a microorganism present in the fermentation and comparing said expression level to a reference level of expression for said nucleic acid molecules, wherein said expression level is indicative of sub-optimal fermentation.

In a second aspect, the invention provides a nucleic acid molecule isolated from yeast or a biologically active fragment thereof, wherein the expression of said nucleic acid is regulated in the presence or absence of zinc.

Preferably, the nucleic acid molecule is genomic DNA, cDNA, RNA, or hybrid molecule thereof. Most preferably, the nucleic acid is a DNA molecule having a nucleotide sequence as shown in FIG. 3.

In a third aspect, the present invention provides a polypeptide or biologically active fragment thereof, wherein the expression of said polypeptide is regulated in the presence or absence of zinc. Preferably, the polypeptide has an amino acid sequence as shown in FIG. 2.

Modified and variant forms of the polypeptide may be produced in vitro by means of chemical or enzymatic treatment or in vivo by means of recombinant DNA technology. Such polypeptides may differ from native zinc-regulated polypeptide, for example, by virtue of one or more amino acid substitutions, deletions or insertions, or in the extent or pattern of glycosylation, but substantially retain a biological activity of native zinc-regulated polypeptide.

In a further preferred embodiment the invention provides a nucleic acid molecule comprising:
  a). a nucleic acid sequence as shown in FIG. 3;
  b). a biologically active fragment of a);
  c). a nucleic acid molecule which has at least 75% sequence homology with any one of the nucleic acid sequences shown in a) or b); or
  d). a nucleic acid molecule that is capable of hybridising to any one of the nucleic acid molecules disclosed in a) or b) under stringent conditions.

While the methods disclosed herein might be used to monitor fermentation using any microorganism it is preferably used to monitor yeast fermentation. Most preferably the microorganism is a brewer's yeast.

It will be further appreciated by those skilled in the art that once a nucleic acid molecule or molecules has/have been identified any number of techniques used to detect nucleic acid expression may be used including Northern hybridisation analysis or dot-blot hybridisation. However, the preferred technique used for identifying nucleic acid expression is real-time PCR.

It will also be appreciated by those skilled in the art that the methods described herein may be used to identify a number of nucleic acids associated with various stress conditions; however, the stress condition which is preferably monitored is zinc-deficiency. In particular the stress-related nucleic acid is either YOR387c or YGL285w.

In a fourth aspect, the present invention provides a nucleic acid isolated from yeast comprising a zinc-control sequence.

In a fifth aspect, the present invention provides a construct comprising a zinc control sequence operatively linked to a nucleic acid molecule, wherein the expression of the nucleic acid molecule is controlled by the control sequence.

Preferably the control sequence is selected from the group consisting of a regulatory element, an enhancer element and a promoter.

In a sixth aspect, the present invention provides a method of controlling the expression of a nucleic acid molecule in an organism comprising the step of transfecting or transforming into said organism a construct comprising a zinc control polynucleic acid sequence operatively linked to the nucleic acid molecule, wherein the expression of the nucleic acid molecule is altered in the presence or absence of zinc.

For the purposes of this specification it will be clearly understood that the word "comprising" means "including but not limited to", and that the word "comprises" has a corresponding meaning.

BRIEF DESCRIPTION OF THE FIGURES

FIG. 2 shows the amino acid sequence comparison (alignment) between cloned YOR387c product (SEQ ID NO:3) (top sequence), cloned YGL258w product (SEQ ID NO:4) (middle sequence) and the S. cerevisiae YGL258w amino acid sequence SEQ ID NO:7 (bottom sequence).

FIG. 3 shows a nucleic acid sequence comparison of YOR387c DNA (SEQ ID NO:5) and YGL258w DNA (SEQ ID NO:6) upstream activating and terminal regions. Appropriate DNA sequences (motifs) involved in the expression of the genes (e.g., TATA box, etc.) are depicted by underlining, and primers used to clone the YOR387c gene are underlined with a double line.

DETAILED DESCRIPTION OF THE INVENTION

Figure 1:
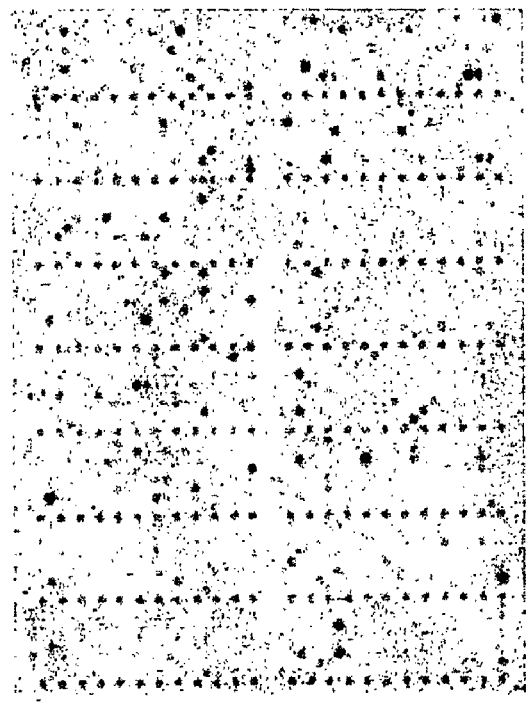
FIG. 1 shows a GeneFilter™ hybridised with cDNA produced from RNA isolated from yeast strains grown in LZMM.

The practice of the present invention employs, unless otherwise indicated, conventional molecular biology, cellular biology, and recombinant DNA techniques within the skill of the art. Such techniques are well known to the skilled worker, and are explained fully in the literature. See, e.g., Sambrook and Russell "Molecular Cloning: A Laboratory Manual" (2001); Cloning: A Practical Approach," Volumes I and II (D. N. Glover, ed., 1985); "Oligonucleotide Synthesis" (M. J. Gait, ed., 1984); "Nucleic Acid Hybridisation" (B. D. Hames & S. J. Higgins, eds., 1985); "Antibodies: A Laboratory Manual" (Harlow & Lane, eds., 1988); "Transcription and Translation" (B. D. Hames & S. J. Higgins, eds., 1984); "Animal Cell Culture" (R. I. Freshney, ed., 1986); "Immobilised Cells and Enzymes" (IRL Press, 1986); B. Perbal, "A Practical Guide to Molecular Cloning" (1984), and Sambrook, et al., "Molecular Cloning: a Laboratory Manual" (1989). Ausubel, F. et al., 1989-1999, "Current Protocols in Molecular Biology" (Green Publishing, New York).

Before the present methods are described, it is understood that this invention is not limited to the particular materials and methods described, as these may vary. It is also to be understood that the terminology used herein is for the purpose of describing particular embodiments only, and is not intended to limit the scope of the present invention which will be limited only by the appended claims. It must be noted that as used herein and in the appended claims, the singular forms "a," "an," and "the" include plural reference unless the context clearly dictates otherwise. Thus, for example, a reference to "a transcript" includes a plurality of such transcripts, and a reference to "a primer" is a reference to one or more primers and equivalents thereof known to those skilled in the art, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

All publications mentioned herein are cited for the purpose of describing and disclosing the microorganisms, protocols, reagents and primers which are reported in the publications and which might be used in connection with the invention. Nothing herein is to be construed as an admission that the invention is not entitled to antedate such disclosure by virtue of prior invention.

In describing the present invention, the following terminology is used in accordance with the definitions set out below.

| ABBREVIATIONS USED | |
|---|---|
| cDNA | Complementary deoxyribonucleic acid |
| CPM | Counts per minute |
| DNA | Deoxyribonucleic acid |
| LZMM | Low zinc medium |
| mRNA | Messenger ribonucleic acid |
| PCR | Polymerase chain reaction |
| RNA | Ribonucleic acid |
| RT-PCR | Reverse-transcriptase polymerase chain reaction. |
| Taq | *Thermophilus aquaticus* |
| $T_m$ | Melting temperature |
| tRNA | Transfer ribonucleic acid |

In a first step of the present invention total RNA is isolated from a microorganism taken from a fermentation process. As used herein, the phrase "fermentation microorganism" means any microorganism that can be used commercially to produce fermentation products, such as for example, alcohol. For example, a fermentation microorganism according to the present invention may include bacterial cells or yeast cells. Accordingly, the microorganism may be selected from *Escherichia, Bacillus, Cyanobacter, Streptomyces, Coryne-* bacteria, *Zymomonas*, *Saccharomyces*, *Zygosaccharomyces* and *Schizosaccharomyces* cells.

As also used herein the term "fermentation process" refers to a process in which one or more substrates are converted by a microorganism or extract of a microorganism to a product, wherein either the product or a by-product of the process is a desirable compound. For example in the process of sugar degradation utilizing a yeast or bacterium, glucose or other saccharides are a substrate, the process is glycolysis (either anaerobic or aerobic), and the desired product is ethanol and/or methanol. In another example, in the process of bread baking, the microorganism is yeast, the substrate includes simple and complex carbohydrates, and the by-product is $CO_2$. Of course a combination of desirable product and by-product are also contemplated, and may include a beer brewing process in which ethanol and $CO_2$ are the desirable product and by-product. Contemplated fermentations may be performed utilizing living cells, dormant cells (e.g., freeze-dried cells), or cell extracts.

Once the fermentation microorganism has been isolated from the fermentation process the total RNA is isolated. The term "RNA" refers to RNA in all its forms including mRNA, tRNA and rRNA. Methods for preparing total RNA are well known in the art and are described generally in textbooks such as Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294-5299).

Once the total RNA has been isolated and/or purified the expression levels of particular genes are detected and/or measured in order to determine whether or not a fermentation process is progressing at a sub-optimal level. The term "detection" refers to any means of detecting the expression of particular genes. For example, known methods of detecting gene expression include, for example, Northern blot analysis, RNase protection assays, or selective hybridization to arrayed cDNA libraries.

In one preferred embodiment cDNA is prepared from the total RNA. The term "cDNA" is included in the terms "nucleic acid molecule" and "polynucleic acid molecule" as these refer to deoxyribonucleic acid and ribonucleic acid in all their forms, i.e., single and double-stranded DNA, cDNA, mRNA, and the like. In particular, cDNA refers to a "double-stranded DNA molecule" comprising the deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments) and plasmids or vectors. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

The methods of producing cDNA are well known in the art see, for example, Okayama and Berg (1982) Mol. Cell. Biol 2, 161; Gubler and Hoffman (1983) Gene 25, 283. Briefly, first strand synthesis is driven by Avian Myeloblastosis virus (AMV) reverse transcriptase and either random hexameric primers or an oligo(dT) primer, followed directly by second strand replacement synthesis using Rnase H and DNA polymerase I. After treatment with T4 DNA polymerase to flush the ends, the double-stranded cDNA molecules are prepared for cloning or can be detected by dot blot analysis.

An alternative procedure utilises the above procedure followed by polymerase chain reaction is procedure is termed "RT-PCR". Essentially, after the cDNA is formed the procedure follows the temperature cycling steps of the basic polymerase chain reaction. "Polymerase chain reaction," or "PCR," as used herein generally refers to a method for amplification of a desired nucleotide sequence in vitro, as described in U.S. Pat. No. 4,683,195. In general, the PCR method involves repeated cycles of primer extension synthesis, using two oligonucleotide primers capable of hybridising preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used. Wang, et al., in PCR Protocols, pp. 70-75 (Academic Press, 1990); Ochman, et al., in PCR Protocols, pp. 219-227; Triglia, et al., *Nuc. Acids Res.* 16:8186 (1988).

As used herein, the term "PCR reagents" refers to the chemicals, apart from the target nucleic acid sequence, needed to perform the PCR process. These chemicals generally consist of five classes of components: (i) an aqueous buffer, (ii) a water soluble magnesium salt, (iii) at least four deoxyribonucleotide triphosphates (dNTPs), (iv) oligonucleotide primers (normally two primers for each target sequence, the sequences defining the 5' ends of the two complementary strands of the double-stranded target sequence), and (v) a polynucleotide polymerase, preferably a DNA polymerase, more preferably a thermostable DNA polymerase, i.e. a DNA polymerase which can tolerate temperatures between 90° C. and 100° C. for a total time of at least 10 minutes without losing more than about half its activity.

The four conventional dNTPs are thymidine triphosphate (dTTP), deoxyadenosine triphosphate (dATP), deoxycitidine triphosphate (dCTP), and deoxyguanosine triphosphate (dGTP). These conventional triphosphates may be supplemented or replaced by dNTPs containing base analogues which Watson-Crick base pair like the conventional four bases, eg deoxyuridine triphosphate (dUTP).

Once the PCR products have been formed these can be analysed by conventional dot blot analysis or the fragments resolved on agarose gels against known standards.

In one particularly preferred embodiment the total RNA is analysed by Northern hybridisation analysis. In this method total RNA is run on a denaturing agarose gel and detected by hybridization of a labelled oligonucleotide probe in the dried gel itself or on a membrane. See, for example, Ausubel supra; Sambrook et al, supra.

Oligonucleotide probes are usually substantially similar such that they hybridise. Two DNA sequences are "substantially similar" when at least about 85%, preferably at least about 90%, and most preferably at least about 95%, of the nucleotides match over the defined length of the DNA. sequences. Sequences that are substantially similar can be identified, for example, in a Northern hybridisation experiment performed under stringent conditions as defined for that particular system. Defining appropriate hybridisation conditions is within the skill of the art. See e.g., Maniatis et al., DNA Cloning, vols. I and II. Nucleic Acid Hybridisation. However, briefly, "stringent conditions" for hybridisation or annealing of nucleic acid molecules are those that (1) employ low ionic strength and high temperature for washing, for example, 0.015M NaCl/0.0015M sodium citrate/0.1% sodium dodecyl sulfate (SDS) at 50° C., or (2) employ during hybridisation a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC and 0.1% SDS.

The invention further relates to nucleotide probes that are sufficiently complementary to regions of contiguous nucleic acid residues within the above-described target DNA to hybridise thereto, preferably under high stringency conditions. Exemplary probes include oligomers that are at least about 15 nucleic acid residues long and that are selected from any 15 or more contiguous residues of DNA of the present invention. Preferably, oligomeric probes used in the practice of the present invention are at least about 20 nucleic acid residues long. The present invention also contemplates oligomeric probes that are 150 nucleic acid residues long or longer. Those of ordinary skill in the art realise that nucleic hybridisation conditions for achieving the hybridisation of a probe of a particular length to polynucleotides of the present invention can readily be determined. Such manipulations to achieve optimal hybridisation conditions for probes of varying lengths are well known in the art. See, e.g., Sambrook et al., *Molecular Cloning: A Laboratory Manual*, Second Edition, Cold Spring Harbor (1989), incorporated herein by reference.

Preferably, oligomeric probes of the present invention are labelled to render them readily detectable. Detectable labels may be any species or moiety that may be detected either visually or with the aid of an instrument. Commonly used detectable labels are radioactive labels such as, for example, $^{32}P$, $^{14}C$, $^{125}I$, $^{3}H$, and $^{35}S$. Examples of fluorescer-quencher pairs may be selected from xanthene dyes, including fluorescein, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoaxazolyl)phenyl)maleimide; benzoxadiazoles, stilbenes, pyrenes, and the like. Most preferably, the fluorescent compounds are selected from the group consisting of VIC, carboxy fluorescein (FAM), Lightcycler 640 and Cy5.

Biotin-labelled nucleotides can be incorporated into DNA or RNA by such techniques as nick translation, chemical and enzymatic means, and the like. The biotinylated probes are detected after hybridisation, using indicating means such as avidin/streptavidin, fluorescent labelling agents, enzymes, colloidal gold conjugates, and the like. Nucleic acids may also be labelled with other fluorescent compounds, with immunodetectable fluorescent derivatives, with biotin analogues, and the like. Nucleic acids may also be labelled by means of attachment to a protein. Nucleic acids cross-linked to radioactive or fluorescent histone single-stranded binding protein may also be used. Those of ordinary skill in the art will recognise that there are other suitable methods for detecting oligomeric probes and other suitable detectable labels that are available for use in the practice of the present invention. Moreover, fluorescent residues can be incorporated into oligonucleotides during chemical synthesis.

In a particularly preferred embodiment the present invention utilises a combined PCR and hybridisation probing system so as to make the most of the closed tube or homogenous assay systems such as the use of FRET probes as disclosed in US patents (U.S. Pat. Nos. 6,140,054; 6,174,670), the entirety of which are also incorporated herein by reference. In one of it's simplest configurations, the FRET or "fluorescent resonance energy transfer" approach employs two oligonucleotides which bind to adjacent sites on the same strand of the nucleic acid being amplified. One oligonucleotide is labelled with a donor fluorophore which absorbs light at a first wavelength and emits light in response, and the second is labelled with an acceptor fluorophore which is capable of fluorescence in response to the emitted light of the first donor (but not substantially by the light source exciting the first donor, and whose emission can be distinguished from that of the first fluorophore). In this configuration, the second or acceptor fluorophore shows a substantial increase in fluorescence when it is in close proximity to the first or donor fluorophore, such as occurs when the two oligonucleotides come in close proximity when they hybridise to adjacent sites on the nucleic acid being amplified (for example in the annealing phase of PCR) forming a fluorogenic complex. As more of the nucleic acid being amplified accumulates, so more of the fluorogenic complex can be formed and there is an increase in the fluorescence from the acceptor probe, and this can be measured. Hence the method allows detection of the amount of product as it is being formed. In another simple embodiment, and as applies to use of FRET probes in PCR based assays, one of the labelled oligonucleotides may also be a PCR primer used for PCR. In this configuration, the labelled PCR primer is part of the DNA strand to which the second labelled oligonucleotide hybridises, as described by Neoh et al (J Clin Path 1999; 52:766-769), von Ahsen et al (Clin Chem 2000; 46:156-161), the entirety of which are encompassed by reference.

It will be appreciated by those of skill in the art that amplification and detection of amplification with hybridisation probes can be conducted in two separate phases—for example by carrying out PCR amplification first, and then adding hybridisation probes under such conditions as to measure the amount of nucleic acid which has been amplified. However, a preferred embodiment of the present invention utilises a combined PCR and hybridisation probing system so as to make the most of the closed tube or homogenous assay systems. Such systems would also be adaptable to the detection methods described here.

It will also be appreciated by those skilled in the art that detection of amplification in homogenous and/or closed tubes can be carried out using numerous means in the art, for example using TaqMan® hybridisation probes in the PCR reaction and measurement of fluorescence specific for the target nucleic acids once sufficient amplification has taken place. However, because of the nature and speed of the Roche Lightcycler®, the preferred method is by using real-time PCR and melting curve analysis on the Roche Lightcycler® using fluorescent labelled hybridisation oligonucleotides.

Those skilled in the art will be aware that other similar quantitative "real-time" and homogenous nucleic acid amplification/detection systems exist such as those based on the TaqMan approach (U.S. Pat. Nos. 5,538,848 and 5,691,146), fluorescence polarisation assays (e.g. Gibson et al., Clin Chem, 1997; 43: 1336-1341), and the Invader assay (e.g. Agarwal P et al., Diagn Mol Pathol 2000 September; 9(3): 158-164; Ryan D et al, Mol Diagn 1999 June; 4(2): 135-144). Such systems would also be adaptable to use the invention described, enabling real-time monitoring of nucleic acid amplification.

"Plasmids" are DNA molecules that are capable of replicating within a host cell, either extrachromosomally or as part of the host cell chromosome(s), and are designated by a lower case "p" preceded and/or followed by capital letters and/or numbers. The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeably with plasmids described herein.

"Control sequences" refers to DNA sequences necessary for the expression of an operably linked nucleotide coding sequence in a particular host cell. The control sequences that are suitable for expression in prokaryotes, for example, include origins of replication, promoters, ribosome binding sites, and transcription termination sites. The control sequences that are suitable for expression in eukaryotes, for example, include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Digestion" of DNA refers to the catalytic cleavage of DNA with an enzyme that acts only at certain locations in the DNA. Such enzymes are called restriction enzymes or restriction endonucleases, and the sites within DNA where such enzymes cleave are called restriction sites. If there are multiple restriction sites within the DNA, digestion will produce two or more linearized DNA fragments (restriction fragments). The various restriction enzymes used herein are commercially available and their reaction conditions, cofactors, and other requirements as established by the enzyme manufacturers are used.

Restriction enzymes commonly are designated by abbreviations composed of a capital letter followed by other letters representing the microorganism from which each restriction enzyme originally was obtained and then a number designating the particular enzyme. In general, about 1 μg of DNA is digested with about 1-2 units of enzyme in about 20 μl of buffer solution. Appropriate buffers and substrate amounts for particular restriction enzymes are specified by the manufacturer, and/or are well known in the art.

"Recovery" or "isolation" of a given fragment of DNA from a restriction digest typically is accomplished by separating the digestion products, which are referred to as "restriction fragments" on a polyacrylamide or agarose gel by electrophoresis, identifying the fragment of interest on the basis of its mobility relative to that of marker DNA fragments of known molecular weight, excising the portion of the gel that contains the desired fragment, and separating the DNA from the gel, for example by electroelution.

"Ligation" refers to the process of forming phospho-diester bonds between two double-stranded DNA fragments. Unless otherwise specified, ligation is accomplished using known buffers and conditions with 10 units of T4 DNA ligase per 0.5 μg of approximately equimolar amounts of the DNA fragments to be ligated.

"Oligonucleotides" are short-length, single- or double-stranded polydeoxynucleotides that are chemically synthesized by known methods (involving, for example, triester, phosphoramidite, or phosphonate chemistry), such as described by Engels, et al., *Agnew. Chem. Int. Ed. Engl.* 28:716-734 (1989). They are then purified, for example, by polyacrylamide gel electrophoresis.

"Zinc-regulated nucleic acid" is RNA or DNA that is substantially similar to the nucleotide sequence shown in FIG. 3 and the expression of the nucleic acid is affected in the presence or absence of zinc. Zinc regulated nucleic acid is obtained from RNA, cDNA or genomic DNA libraries, or by in vitro synthesis. Identification of zinc regulated nucleic acid within a cDNA or a genomic DNA library, or in some other mixture of various nucleic acids, is conveniently accomplished by the use of an oligonucleotide hybridization probe that is labelled with a detectable moiety, such as a radioisotope. Keller, et al., DNA Probes, pp. 149-213 (Stockton Press, 1989). To identify nucleic acid encoding zinc regulated nucleic acid, the nucleotide sequence of the hybridization probe preferably is selected so that the hybridization probe is capable of hybridizing to zinc regulated nucleic acid that has the nucleotide sequence set forth in FIG. 3, or a variant or derivative thereof as described herein, under the hybridization conditions chosen. Another method for obtaining zinc regulated nucleic acid is to chemically synthesize it using one of the methods described, for example, by Engels, et al., *Agnew. Chem. Int. Ed. Engl.* 28:716-734 (1989).

If the entire nucleotide coding sequence for zinc regulated nucleic acid is not obtained in a single cDNA, genomic DNA, or other DNA, as determined, for example, by DNA sequencing or restriction endonuclease analysis, then appropriate DNA fragments (e.g., restriction fragments or PCR amplification products) may be recovered from several DNAs and covalently joined to one another to construct the entire coding sequence. The preferred means of covalently joining DNA fragments is by ligation using a DNA ligase enzyme, such as T4 DNA ligase.

"Isolated" zinc regulated nucleic acid is zinc regulated nucleic acid that is identified and separated from (or otherwise substantially free from), contaminant nucleic acid encoding other polypeptides. The isolated zinc regulated nucleic acid can be incorporated into a plasmid or expression vector.

Nucleotide sequence variants of zinc regulated nucleic acid is prepared by a variety of methods known in the art. These methods include, but are not limited to, isolation from a natural source (in the case of naturally occurring nucleotide sequence variants of zinc regulated nucleic acid) or preparation by site-directed (or oligonucleotide-mediated) mutagenesis, PCR mutagenesis, and cassette mutagenesis of an earlier prepared DNA encoding a variant or a non-variant form of zinc regulated nucleic acid.

Site-directed mutagenesis is a preferred method for preparing substitution, deletion, and insertion variants of zinc regulated nucleic acid. This technique is well known in the art, Zoller, et al., *Meth. Enz.* 100:4668-500 (1983); Zoller, et al., *Meth. Enz.* 154:329-350 (1987); Carter, *Meth. Enz.* 154:382-403 (1987); Horwitz, et al., *Meth. Enz.* 185:599-611 (1990), and has been used, for example, to produce amino acid sequence variants of trypsin and T4 lysozyme, which variants have certain desired functional properties. Perry, et al., *Science* 226:555-557 (1984); Craik, et al., *Science* 228:291-297 (1985).

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang, et al., *Meth. Enzymol.* 68:90-98 (1979); Brown, et al., *Meth. Enzymol.* 68:109-151 (1979); Caruther, et al., *Meth. Enzymol.* 154:287-313 (1985). The general approach to selecting a suitable hybridization probe or primer is well known. Keller, et al., DNA Probes, pp. 11-18 (Stockton Press, 1989). Typically, the hybridization probe or primer will contain 10-25 or more nucleotides, and will include at least 5 nucleotides on either side of the sequence encoding the desired mutation so as to ensure that the oligonucleotide will hybridize preferentially to the single-stranded DNA template molecule.

"Expression" refers to transcription and/or translation. "Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase.

As used herein, the terms "transformation" and "transfection" refer to the process of introducing a desired nucleic acid, such a plasmid or an expression vector, into a host cell. Various methods of transformation and transfection are available, depending on the nature of the host cell. In the case of E. coli cells, the most common methods involve treating the cells with aqueous solutions of calcium chloride and other salts. In the case of mammalian cells, the most common methods are transfection mediated by either calcium phosphate or DEAE-dextran, or electroporation. Sambrook, et al., eds., Molecular Cloning, pp. 1.74-1.84 and 16.30-16.55 (Cold Spring Harbor Laboratory Press, 1989). Following transformation or transfection, the desired nucleic acid may integrate into the host cell genome, or may exist as an extrachromosomal element.

Host cells that are transformed or transfected with the above-described plasmids and expression vectors are cultured in conventional nutrient media modified as is appropriate for inducing promoters or selecting for drug resistance or some other selectable marker or phenotype. The culture conditions, such as temperature, pH, and the like, suitably are those previously used for culturing the host cell used for cloning or expression, as the case may be, and will be apparent those skilled in the art.

Suitable host cells for cloning or expressing the vectors herein are prokaryotes, yeasts, and higher eukaryotes, including insect, vertebrate, and mammalian host cells. Suitable prokaryotes include eubacteria, such as Gram-negative or Gram-positive organisms, for example, *E. coli, Bacillus* species such as *B. subtilis, Pseudomonas* species such as *P. aeruginosa, Salmonella typhimurium*, or *Serratia marcescans*.

In addition to prokaryotes, eukaryotic microbes such as filamentous fungi or yeast are suitable hosts for vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, Beach and Nurse, *Nature* 290:140-142 (1981), *Pichia pastoris*, Cregg, et al., *Bio/Technology* 5:479-485 (1987); Sreekrishna, et al., *Biochemistry* 28:4117-4125 (1989), *Neurospora crassa*, Case, et al., *Proc. Natl. Acad. Sci. USA* 76:5259-5263 (1979), and Aspergillus hosts such as *A. nidulans*, Ballance, et al., *Biochem. Biophys. Res. Commun.* 112:284-289 (1983); Tilburn, et al., *Gene* 26:205-221 (1983); Yelton, et al., *Proc. Natl. Acad. Sci. USA* 81:1470-1474 (1984), and *A. niger*, Kelly, et al., *EMBO J.* 4:475-479 (1985).

Although the invention has been described with reference to presently preferred embodiments, it should he understood that various modifications can be made without departing from the spirit of the invention. Moreover, the following examples are offered by way of illustration only and are not intended to limit the invention in any manner. All patent and literature references cited herein are expressly incorporated.

Example 1

Isolation of Nucleic Acids Associated with Fermentation

To determine the usefulness of whole-genome expression analysis in monitoring yeast gene expression during industrial processes a 200 litre yeast culture was inoculated with a brewing yeast obtained from Carlton and United Breweries (Abbotsford, Victoria, Australia). Yeast were grown in low zinc medium (LZMM) prepared essentially as described in Zhao and Eide (1996), except that maltose replaced glucose as the carbon source A yeast colony was inoculated into LZMM supplemented with 4 mg/l zinc and grown overnight at 30° C. with shaking. Cells were harvested and washed three times with SDW before inoculation at an optical density ($OD_{600}$) of 0.1 into LZMM with and without supplemental zinc. Cells were harvested for RNA isolation at either an ($OD_{600}$) of 0.5 or after 1 h and 23 h post inoculation.

Total RNA for Northern hybridisation and Microarray analysis was isolated from yeast cells using TRIZOL® reagent (Life Technologies Inc., Gaithersburg, Md. 20884, USA) according to the manufacturer's instructions.

Labelled cDNA ($^{33}P$) was prepared from 10 µg of total RNA (manufacturer's recommended amount and amount used in previous tests using laboratory conditions and medium).

Microarray analysis was carried out using GeneFilters® (Research Genetics) containing over 6,000 yeast genes. They were hybridised with cDNA produced from total RNA according to the manufacturer's instructions (Research Genetics). Images indicating gene expression on the GeneFilters® were obtained on a PhosphorImager (Molecular Dynamics) using ImageQuaNT v4.2a software.

Electrophoretic analysis of the total RNA showed that the ratio of ribosomal RNA to mRNA was high and a larger than normal amount of small molecular weight species, possibly tRNA, was present (results not shown). To confirm that RNAase contamination was not responsible, total RNA was re-isolated from industrial samples at the same time and with the same materials as laboratory grown yeast. These results suggested that there was no RNAase activity and the above observations were correct. A more representative cDNA probe was obtained by increasing the total RNA amount to 10 µg in the standard reaction. The labelled cDNA was hybridised to GeneFilters® and radiation emissions were quantified to provide a quantitative measure of the relative abundance of mRNA levels. Although hybridisation was not highly efficient, 3 day exposures allowed for the identification of differentially expressed genes (FIG. 1).

The applicant has therefore demonstrated that yeast genome-wide transcriptional analysis technology can readily identify the differential expression of genes under varying fermentation conditions. A family of genes involved in lipid, fatty-acid and sterol metabolism were more highly expressed in the initial phases of fermentation than after 23 hours (Table 1).

TABLE 1

Genes up-regulated in the first hour of fermentation compared to the 23$^{rd}$ hour.

| Fold induction | Locus name | Gene name | Characteristics |
|---|---|---|---|
| Unsaturated Fatty acid synthesis | | | |
| 49 | YGL055w | OLE1 | induced by Cox5Bp, Stearoyl-CoA desaturase |
| Ergosterol synthesis | | | |
| 10 | YMR015c | ERG5 | Cytochrome P450 |
| 18 | YHR007c | ERG11 | catalyzes the 14-alpha demethylation of lanosterol |
| 11 | YGL001c | ERG26 | C-3 sterol dehydrogenase, C-4 decarboxylase |
| 7 | YML126c | ERG13 | converts acetoacetyl-CoA to hydroxymethylglutaryl-CoA |
| 27 | YPL028w | ERG10 | Acetyl-CoA acetyltransferase |
| 5 | YGR175c | ERG1 | converts squalene & O2 into squalene-2,3-epoxide and H$_2$O |
| 5 | YGR060w | ERG25 | oxidizes 4,4-dimethylzymosterol to carboxylic acid |
| 3 | YLR056w | ERG3 | C5 = 6 desaturation |
| Roles in lipid, fatty-acid and sterol metabolism | | | |
| 95 | YPL061w | ALD6 | Acetyl-CoA production |
| 21 | YPR065w | ROX1 | represses ERG11, OLE1 and COX5B |
| 6 | YKL032c | IXR1 | Represses COX5A |
| 29 | YER141w | COX15 | cytochrome oxidase assembly |
| 13 | YPL117c | IDI1 | cholesterol biosynthesis pathway |
| 7 | YLL013c | | modulation of the poly(A) status of COX17 mRNA |
| 19 | YHR179w | OYE2 | may be involved in sterol metabolism |
| Oxidative stress and STRE induced genes | | | |
| 15 | YER150w | SPI1 | has 62% identity to Sed1p |
| 10 | YGR088w | CTT1 | detoxification of superoxide radicals and H$_2$O$_2$ |
| 44 | YLR249w | YEF3 | contains STRE elements |
| 54 | YDR353w | TRR1 | Thioredoxin reductase |
| 29 | YDR502c | SAM2 | Involved with CYS3 |
| 14 | YAL012w | CYS3 | Cystathionine gamma-lyase, generates cysteine |
| 41 | YDR077w | SED1 | serves a role in protection from oxidative stress |
| 10 | YGR086c | | induced by pH and salt |
| 9 | YMR002w | | expressed under the same conditions as SED1, SPI1 |
| Other | | | |
| 5 | YPL089c | RLM1 | Transcription factor of the MADS |
| 7 | YMR043w | MCM1 | Induced by the SWI-SNF complex |
| 6 | YBR289w | SNF5 | Part of the SWI-SNF complex |
| 9 | YGR160w | | same expression as RHR2 |
| 11 | YIL053w | RHR2 | involved in cellular production of glycerol |
| 51 | YMR011w | HXT2 | High-affinity hexose transporter |
| 7 | YBR113w | | unknown |
| 10 | YDR505c | PSP1 | unknown |
| 6 | YGL122c | NAB2 | polyadenylation of pre-mRNA and for mRNA export |
| 13 | YOR302w | | mediates translational regulation |
| 12 | YKL054c | VID31 | Vacuole Import and Degradation |
| 29 | YBR105c | VID24 | Vacuole Import and Degradation |

The highest differentially expressed of these genes was OLE1. The Ole1p converts saturated fatty acids and oxygen to unsaturated fatty acids (Fujiwara et al 1998) and expression is activated by hypoxia, early cell cycle and saturated fatty acids (Choi et. al., 1996; Choi et. al., 1998). These expression characteristics are similar to ERG11, which is one of eight genes contained in these results (Table 1) that are required for the synthesis of ergosterol (Daum et. al., 1998). This step is the rate-limiting enzyme of this pathway (van den Brink et. al., 1998) and apart from having similar activation characteristics as OLE1, both genes are repressed by the transcription factor ROX1 (Nakagawa et. al., 2001), which is also up-regulated in the first hour. Other genes that are highly expressed in conjunction with the lipid, fatty-acid and sterol metabolism genes are ALD6, a gene that plays a role in the production of cytosolic acetyl-CoA, and IDI1 that has high homology to the human gene of the same name which is involved in the cholesterol synthesis pathway. Oxidative stress response in first hour of fermentation OYE2, another gene whose product is thought to be involved in sterol metabolism (Stott et al., 1993) catalyzes the NADPH-dependent reduction of olefinic bonds of alpha, beta-unsaturated carbonyls, such as in morphinone, 4,4-dimethyl-2-cyclohexenone, or 2-cyclohexenone and may play a role in the metabolism of oxylipins (Schaller et al 1997). Its upstream region has a putative Yap1p binding site and its expression is up-regulated when Yap1p is over-expressed (DeRisi et al 1997). Yap1p is required for activity of the stress response (STRE) element (CCCCT) in response to oxidative stress but does not bind the STRE directly. Other genes in these results that contain (STRE) elements in their upstream activating sequences are SPI1, CTT1, YEF3, TRR1, and CYS3. SPI1 encodes for a cell wall bound protein that has 62% identity to SED1 (Puig et al 1999) another gene that serves a role in protection from oxidative stress (Ezaki). The activation of CYS3 (Table 1) expression also indicates the presence of oxidative stress in the first hour of fermentation. Levels are activated by the presence of the oxidant H$_2$O$_2$. The Cys3p (cysteine desulfhydrase) generates cysteine from cystathionine an important precursor to the generation of the oxidative stress protectant, glutathione.

Example 2

Identification of Zinc-Deficiency Responsive Nucleic Acids

In microarray GeneFilters® results, YOR387c and YGL258w were expressed approximately 300-fold higher in zinc deficient conditions. This increase was about 40-fold higher than the known zinc responsive genes ZAP1 and ZRT1.

Figure 4:
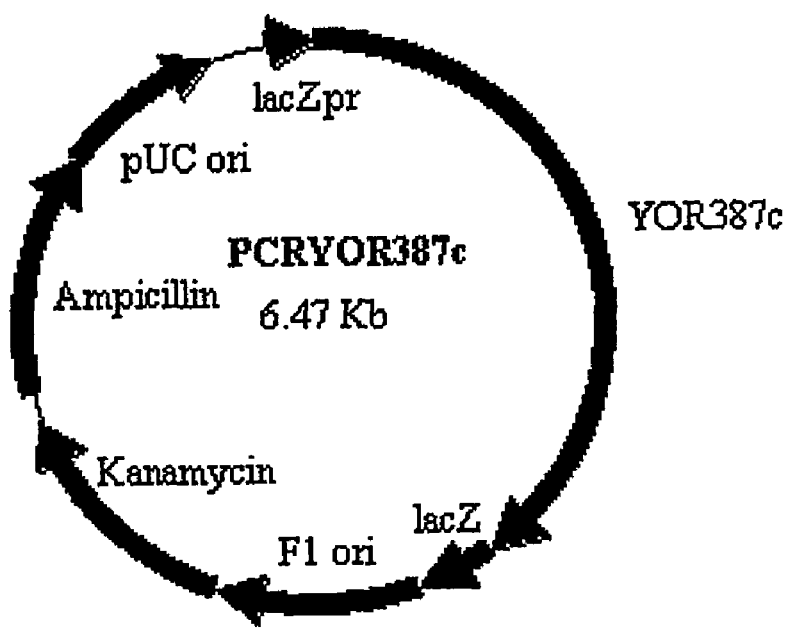
FIG. 4 shows a schematic representation of the plasmid PCR2.1-YOR387c.

Sequence analysis YOR387c and YGL258w showed that these two sequences had 93% predicted amino acid sequence homology and had a 74% amino acid sequence homology with the *Saccharomyces pombe* proteins SPAC977.05, SPAC1348.06c and SPBPB2B2.15. These genes have no known function in their respective cells and have little similarity to any higher eukaryotic genes. To establish whether the regulation of YOR387c and YGL258w was suitable for efficient monitoring of zinc deficient conditions in industrial processes, a DNA probe was developed for Northern analysis of mRNA expression levels. With the high homology of the proteins encoded by YOR387c and YGL258w, differing by only 15 amino acids (FIG. 2) a probe that is specific for either transcript was not possible. Although there are two changes in the upstream activating region none occur within elements known to be important for transcriptional activation (FIG. 3), therefore it would be expected that both genes are expressed in a similar fashion. The sequence at the terminal end of the genes diverge rapidly and this region was used to generate a reverse primer for the cloning of the YOR387c gene. The predicted size of the PCR product using the primers YOR387cF and YOR387cR was 2575 bp and, as expected, a product of approximately 2500 bp was obtained. The 3' A overhang left by the PCR reaction was used to ligate the PCR product into the pCR® 2.1 vector creating the plasmid PCRYOR387c (FIG. 4). The DNA used as a probe to hybridise to YOR387c and YGL258w mRNA was obtained by gel purification of a 378bp fragment created by digesting PCRYOR387c with AccI and NheI restriction enzymes.

Example 3

PCR Cloning of YOR387c

Forward primer for amplification of YOR387c gene by PCR was:
YOR387c-F

```
                                            (SEQ ID NO.: 1)
5' - ATAAGAATGCGGCCGCTGTTTTGGCGTATTCTCCAC - 3'
```
and
reverse primer was YOR387c-R:
```
                                            (SEQ ID NO.: 2)
5' - CCGCTCGAGAACACGCG TAATTGAAAGGG - 3'.
```

The PCR used Tag DNA polymerase (Stratagene) and 100 µl reactions were prepared in accordance with the manufacturer's instructions. The PCR product was ligated into the pCR® 2.1 vector in accordance with the manufacturer's instructions (InVitrogen).

Example 4

Analysis of Zinc Regulated Nucleic Acid

Figure 5:
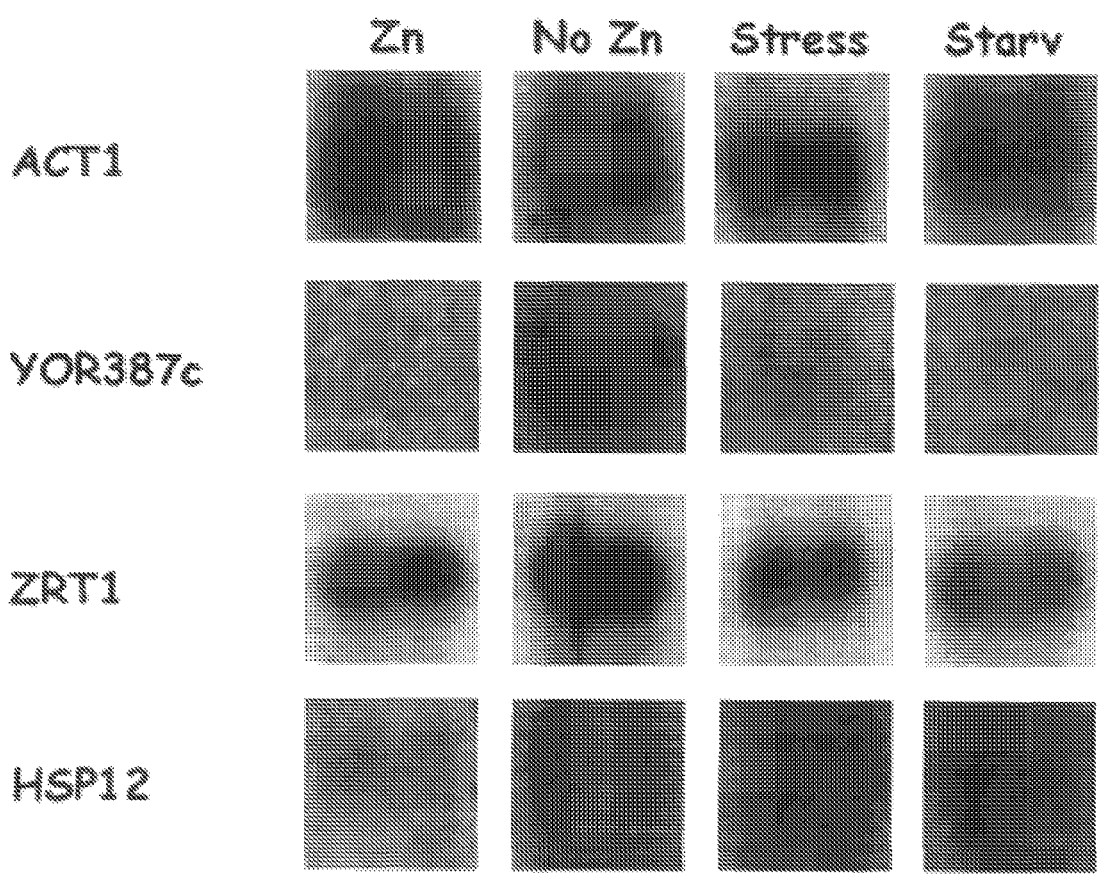
FIG. 5 shows a Northern analysis of YOR387c, ZRT1, HSP12 and ACT1 expression in no zinc (LZMM), zinc (LZMM+4 mg/l zinc), stress (LZMM+4 mg/l zinc+2 mM $H_2O_2$) and starvation (LZMM+4 mg/l zinc with no maltose added) conditions.

To confirm the GeneFilters® expression results, YOR387c/YGL285w expression levels were measured by Northern analysis of total RNA isolated from yeast grown in zinc deficient and zinc replete conditions. The transcript levels using the YOR387c probe were very high in zinc deficient conditions whereas in medium containing zinc the transcript levels were not detectable (FIG. 5). ZRT1, a gene known to be induced in response to zinc deficient conditions was also increased. To determine whether the increase in expression of YOR387c/YGL258w was specific for zinc deficiency and not a general stress response, gene expression was also tested under oxidative stress and carbon starvation conditions. YOR387c/YGL285w and ZRT1 expression levels were responsive only to the zinc depleted conditions, whereas HSP12 expression was high in all conditions tested except in the control medium that had added zinc (FIG. 5). As expected, ACT1 transcript, a commonly used control for standardising RNA concentration, were similar in all conditions (FIG. 5). Taken together these results show that YOR387c/YGL258w are highly expressed in response to and specific for zinc deficient conditions.

References cited herein are listed on the following pages, and are incorporated herein by this reference.

REFERENCES

Bromberg, S. K., Bower, P. A., Duncombe, G. R., Fehring, J., Gerber, L., Lau, V. K., and Tata M. (1997). Requirements for Zinc, Manganese, Calcium, and Magnesium in Wort. J. Am. Soc. Brew. Chem., 55, 123-128.

Cho, R. L, Campbell, M. L, Winzeler, E. A., Steinmetz, L., Conway, A., Wodicka, L., Wolfsberg, T. G., Gabrielian, A. E., Landsman, D., Lockhart, D. L, and Davis, R. W. (1998). A genome-wide transcriptional analysis of the mitotic cell cycle. Mol Cell, 2, 65-73.

Choi, J. Y., Stukey, L, Hwang, S. Y., and Martin, C. E. (1996). Regulatory elements that control transcription activation and unsaturated fatty acid-mediated repression of the Saccharomyces cerevisiae OLE1 gene. J Biol Chem., 271, 3581-9.

Daum, G., Lees, N. D., Bard, M. and Dickson, R. (1998). Biochemistry, Cell Biology and Molecular Biology of Lipids of Saccharomyces cerevisiae. Yeast, 14, 1471-1510.

DeRisi, J. L., Iyer, V. R., and Brown, P. O. (1997). Exploring the metabolic and genetic control of gene expression on a genomic scale. Science, 278, 680-686.

Fujiwara, D., Yoshirnoto, R, Sone, R, Harashima S. and Tamai, Y. (1998). Transcriptional Co-regulation of Saccharomyces cerevisiae Alcohol Acetyltransferase Gene, ATF1 and Ä-9 Fatty Acid Desaturase Gene, OLE1 by Unsaturated Fatty Acids. Yeast, 14, 711-721.

Ivorra, C, Perez-Ortin, J. E, del Olmo, M. (2000). An inverse correlation between stress resistance and stuck fermentations in wine yeasts. A molecular study. Biotechnol and Bioengineering. 64, 698-708.

Nakagawa, Y, Sugioka, S, Kaneko, Y, and Harashima, S. (2001). O2R, a novel regulatory element mediating Rox1p-independent O(2) and unsaturated fatty acid repression of OLE1 in Saccharomyces cerevisiae. J. Bacteriol., 183, 745-751.

Oteiza, P. L, Clegg, M. S., Zago, M. P., Keen, C. L. (2000). Free Radical Biology & Medicine, 28, 1091-1099.

Puig, S., and Perez-Ortin, J. E. (2000). Stress response and expression patterns in wine fermentations of yeast genes induced at the diauxic shift. Yeast, 16, 139-148.

Schaller F, Weiler E W. (1997). Molecular cloning and characterization of 12-oxophytodienoate reductase, an enzyme of the octadecanoid signaling pathway from Arabidopsis thaliana. Structural and functional relationship to yeast old yellow enzyme. J. Biol. Chem., 272, 28066-72.

Stott K, Saito K, Thiele D J, Massey V. (1993). Old Yellow Enzyme. The discovery of multiple isozymes and a family of related proteins. J Biol Chem., 2680, 6097-106 van den Brink, H. M., van Gorcom, R. F., van den Hondel, C. A., and Punt, P. J. (1998). Cytochrome P450 enzyme systems in fungi. Fungal Genet. Biol. 23, 1-17.

Zhao, H. and Eide, D. J. (1997). Zap1p, a metalloregulatory protein involved in zinc responsive transcriptional regulation in Saccharomyces cerevisiae. Mol Cell Biol. 17, 5044-52.

The claims defining the invention are as follows:

1. A method of monitoring fermentation conditions in a zinc-sensitive beer-brewing fermentation process which is suboptimal in the absence of zinc, comprising detecting in S. cerevisiae cells undergoing said beer-brewing fermentation process the expression of
   (i) S. cerevisiae nucleic acid YOR387c which encodes a protein of the sequence SEQ ID NO:3; or
   (ii) S. cerevisiae nucleic acid YGL258w which encodes a protein of the sequence SEQ ID NO:4,
wherein expression of either of said nucleic acid YOR387c or said nucleic acid YGL258w occurs in the absence of zinc and is undetectable in the presence of zinc, so that
   (A) undetectable expression from either of said nucleic acid YOR387c or said nucleic acid YGL258w by Northern hybridization analysis, dot-blot hybridization or real-time PCR indicates the presence of zinc, whereas
   (B) detection of expression of either of said nucleic acid YOR387c or said nucleic acid YGL258w by Northern hybridization analysis, dot-blot hybridization or real-time PCR indicates the absence of zinc and, therefore, suboptimal fermentation conditions.

2. The method according to claim 1, wherein the detecting of expression comprises measuring the presence of an RNA molecule transcribed from YOR387c or YGL258w coding nucleic acid.

3. The method according to claim 1, wherein said nucleic acid YOR387c or said nucleic acid YGL258w is endogenous to the cells in which the fermentation process is being monitored.

* * * * *